US00PP18289P3

(12) United States Plant Patent
Krasinsky

(10) Patent No.: US PP18,289 P3
(45) Date of Patent: Dec. 11, 2007

(54) BOXWOOD CULTIVAR NAMED 'ARCTIC EMERALD'

(50) Latin Name: *Buxus sempervirens*
Varietal Denomination: Arctic Emerald

(76) Inventor: Marlene M. Krasinsky, 1104 Pacific Ave., Brackenridge, PA (US) 15014

( * ) Notice: Subject to any disclaimer, the term of this patent is extended or adjusted under 35 U.S.C. 154(b) by 0 days.

(21) Appl. No.: 11/182,688

(22) Filed: Jul. 15, 2005

(65) Prior Publication Data

US 2007/0016989 P1 Jan. 18, 2007

(51) Int. Cl.
*A01H 5/00* (2006.01)

(52) U.S. Cl. ..... Plt./226
(58) Field of Classification Search ..... Plt./226
See application file for complete search history.

*Primary Examiner*—Kent Bell
*Assistant Examiner*—Louanne Krawczewics Myers
(74) *Attorney, Agent, or Firm*—Kirkpatrick & Lockhart Preston Gates Ellis LLP

(57) ABSTRACT

A new and distinct *Buxus* cultivar is provided. The attractive evergreen hedge/shrub displays a dense columnar, somewhat pyramidal, upright growth habit, and is particularly fast growing relative to many other *Buxus* variants. No pruning is required to maintain the attractive growth habit. The new variant commonly displays a single sturdy trunk or a multi-trunk base, depending on the cutting at time of propagation, that develops multiple pliable fast-growing branches with glossy deep green foliage. The foliage displays deep green color in all weather conditions, temperatures, and degrees of sunlight and shade. The new variant exhibits excellent endurance to both high and low temperatures, and has exceptional tolerance to wind, snow, and ice due in part to the yielding characteristic of its branches. No typical boxwood fragrance is emitted by the foliage or branches. The new variant's growth habit and shape make it suitable for a multitude of landscape and other uses.

11 Drawing Sheets

Figure 1:
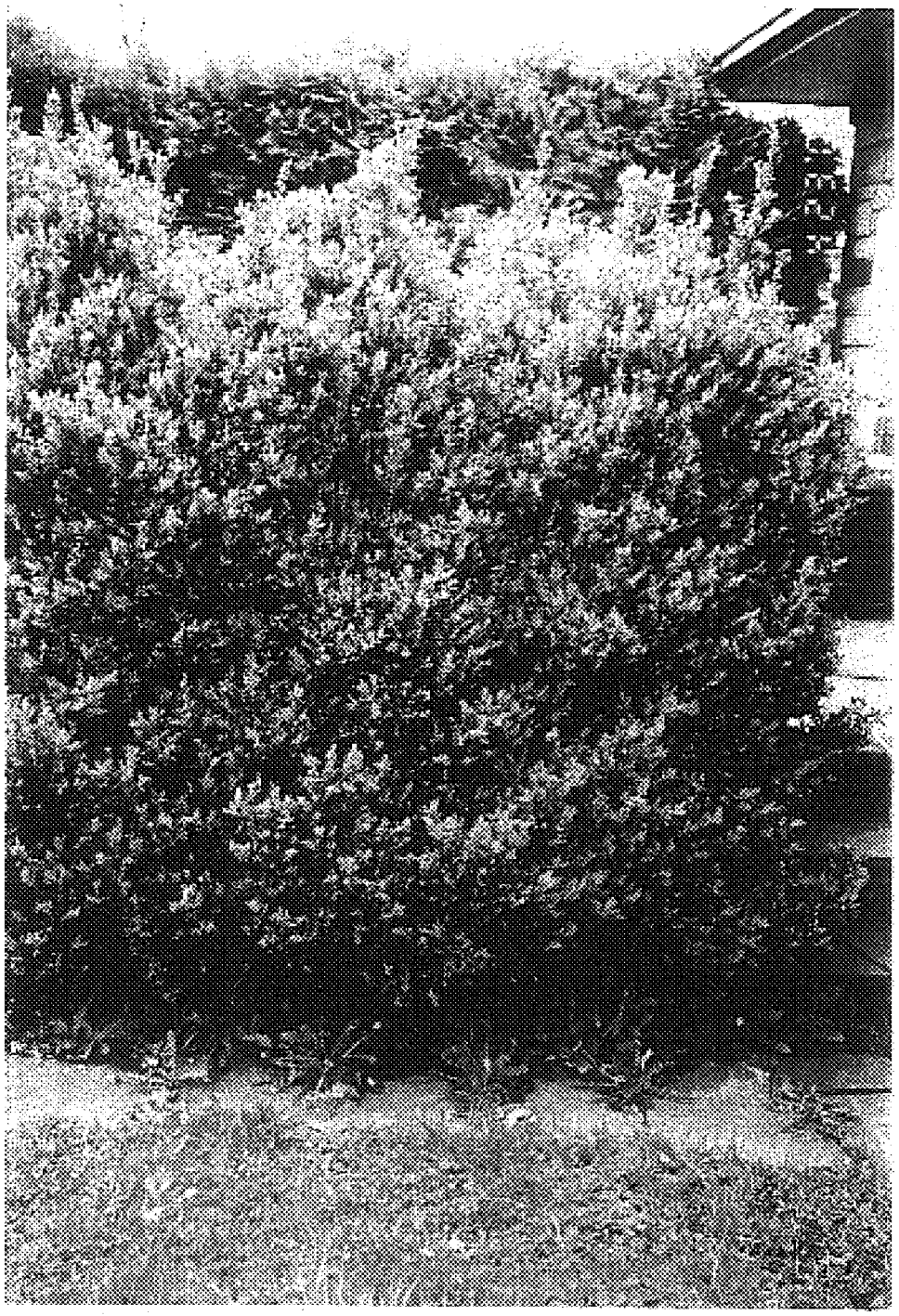

Genus/species: *Buxus sempervirens.*
Varietal denomination: 'Arctic Emerald'.

SUMMARY OF THE INVENTION

The present disclosure relates to a new and distinct *Buxus* cultivar that was discovered in nature around 1993 in Brackenridge, Pa., and was selected and asexually propagated. The parentage of the new cultivar is uncertain. However, it may be the result of a naturally occurring whole plant mutation of an existing but unidentified *Buxus* variety (unpatented).

A single plant of the new cultivar was asexually propagated, selected, and preserved having the distinctive characteristics discussed hereinafter. Had the new cultivar of the present invention not been propagated and preserved, it would not have been available to mankind.

Upon careful observation and testing, the new cultivar of the present invention was found to express the following combination of characteristics:

(a) assumes a dense, columnar, somewhat pyramidal, upright growth habit;

(b) lacks typical boxwood foliage fragrance;

(c) exhibits an unusually rapid growth cycle following asexual propagation from a cutting;

(d) exhibits an exceptionally strong and hardy root system;

(e) exhibits glossy deep olive green foliage throughout the year in high and low temperatures, and does well in full sun, partial sun, and shade, without any substantial change in coloration during the winter;

(f) exhibits excellent all-season hardiness to at least U.S.D.A. Plant Hardiness Zone 5, and likely to Zone 4; and (g) exhibits exceptional tolerance to wind, ice and snow due, at least in part, to the yielding character of its pliable branches.

The new cultivar is a dense upright columnar, somewhat pyramidal, broadleaf evergreen that is capable of being grown and maintained as an attractive ornamental outdoor plant throughout the year. A ratio of height to width of approximately 7:3 is common in older plants. To date, the typical size of fully mature plants is unknown. The new cultivar typically displays a single sturdy base or a multi-trunk base, depending on the cutting at the time of propagation, that develops abundant slender fast-growing compact pliable multi-budded branches. It is fast growing, and two-year old plants, growing in optimal soil conditions, have exhibited up to about 24 inches of new upright branches. Nursery stock may be started in containers, and at from 2 to 5 years old will be of sufficient size for the sales market. 8-month old established cuttings can be planted in the ground, typically without protection, and ready for the sales market in about 1 year, although such plants necessarily will be rather small.

The foliage is found to be lacking in typical boxwood fragrance, and such an absence of fragrance is preferred by some growers. Also, as with other boxwood cultivars, birds, rabbits, and deer tend to dislike and are repelled by the foliage and branches of the new cultivar.

The glossy, deep green foliage is maintained throughout the year, even through the winter. The new cultivar resists a common tendency of certain known boxwood cultivars to assume a brownish-green coloration during the winter, and the new cultivar has been shown to display a glossy deep green coloration even in single digit (Fahrenheit) temperatures. The new cultivar exhibits a light bronze olive green in times of winter thaws, and exhibits deep green coloration in extreme hot and cold weather (see, for example, FIG. 5).

The new cultivar has demonstrated exceptional all-weather hardiness, as well as extraordinary tolerance to wind, ice, and snow, which is at least in part due to its strong and hardy root system and pliable, yielding character of its branches. It has been shown to have exceptional winter tolerance to at least U.S.D.A. Plant Hardiness Zone 5, and probably is hardy to Zone 4. Good resistance to winter burn also is exhibited. The new cultivar does not require protection throughout the range of typical weather conditions during the year. The foliage of the new cultivar exhibits tones of olive green during winter temperature changes. The hardiness of the new cultivar equals or exceeds that of previously known boxwood cultivars known for superior hardiness. Its strong columnar growth habit keeps its general shape, without pruning, in all seasons. Even though severe weather conditions may cause the plants to bend over, the plants spring back into shape after, for example, snow and/or ice on the plants melts (for example, compare FIG. 2 versus FIG. 1). In comparison, *Buxus sempervirens* 'Graham Blandy' (unpatented in the United States), likely hardy to U.S.D.A. Hardiness Zone 5, which has a straight-sided narrow growth habit, may require pruning to maintain its slender shape after Spring growth, when rains sometimes pull down the new growth.

The new cultivar is exceptionally sturdy, withstanding cold temperatures, snow, and ice. The plants typically rebound without damage to the multiple pliable branches of its columnar, somewhat pyramidal growth habit. The new cultivar's Spring growth yields without damage to its form during rains, and requires no pruning during rains. This may be contrasted with the 'Graham Blandy' boxwood, which has branches that tend to fall during heavy rains, and which may require pruning after rains to retain its characteristic slender sides.

The new cultivar can be grown to advantage as attractive ornamentation in various landscapes, and is particularly well suited for use in the formation of a privacy hedge, or privacy wall, due to its dense foliage, rapid upright growth habit, columnar, somewhat pyramidal shape, and height. Its exceptional growth habit, density, and columnar, somewhat pyramidal shape do not require pruning, although it may be pruned to suit particular landscape needs. The new cultivar would do well as single plants and as multiple-plant groupings in landscaping around commercial and residential structures due to its rapid growth habit and columnar, somewhat pyramidal shape relative to other boxwood variants having less upright shapes. The new cultivar's rapid growth habit and columnar, somewhat pyramidal shape makes it suitable for various uses because it adapts well in sun, partial sun, and shade. Its branches are strong and flexible, withstanding heavy rain, ice, and snow, making at adaptable to and exhibiting good growth in north, south, east and west exposures, and avoiding the necessity for covering the plants during severe weather. This contrasts with, for example, *Buxus sempervirens* 'Green Velvet' (unpatented in the United States), which is relatively less dense and which, when planted with a southern exposure, is prone to slower growth, achieving less height and width. Also, in comparison to the new cultivar, the 'Graham Blandy' boxwood does not grow well in full sun. The new cultivar is suitable for various types of border plantings, including low and high landscape borders, and as an enhancement to other plants, including, for example, flowering plants and evergreens of other green to blue hues. Much of the plant displays foliage that has rounded-tip leaves, but as the plant ages spear-like leaves also may be displayed. The compactness and density of the new variant's small broad-leaf rounded tip and spear-like tip foliage make it a suitable choice for topiaries. The new variant's glossy deep green broad-leaf rounded tip and spear-like tip foliage distinguish it from many known boxwood varieties, including *Buxus sempervirens* 'Richard' (unpatented), which has deep green heart-shaped leaves.

The new cultivar has been tested at Brackenridge, Pa. and Natrona Heights, Pa. since 1993, and at West Grove, Pa. since 2001. The new cultivar also has been tested, and its hardiness and other properties observed, in all season weather conditions in the states of California, Maryland, Michigan, North Carolina, Ohio, Oklahoma, Oregon, and Washington, as well as in the District of Columbia, France and The Netherlands since 2001-2002 and up to the present. It has been observed that 'Arctic Emerald' plants include both spear-shaped leaves and rounded oval-like leaves, including some oval-like leaves including an indentation in the top center of the leaves. In contrast, English boxwood includes rounded leaf tips sometimes, but not always, having a split in the top center of the leaf. 'Arctic Emerald' has exhibited a fast, tall growth habit, while English boxwood generally exhibits a slower, shorter growth habit.

When compared with the 'Graham Blandy' boxwood, which is a straight-sided narrow tall upright plant with a narrow base and is likely hardy to U.S.D.A. Plant Hardiness Zone 5, the new cultivar exhibits a tall columnar habit with a relatively wide base, is likely hardy to Zone 4, and has achieved a height of 7½ feet and width of 36 inches feet at 11 years and 4 months (see, for example, FIG. 1). The new cultivar exhibits extraordinary growth without pruning, and pruning is not required to maintain the shape of the plants in harsh weather conditions. The new cultivar has been raised outdoors from 2½ inch plant cuttings in Zone 5 without protection and with, at times, temperatures comparable to Zone 4. Certain specimens of the new cultivar have exhibited accelerated growth after 8 years.

*Buxus sempervirens* 'Arctic Emerald' displays deep green, dense foliage with a fast growing habit withstanding high and low temperatures in U.S.D.A. Plant Hardiness Zone 5, with possible hardiness to Zone 4. The new variety does well in full sun, partial sun, and shade. It is suitable where privacy is desired and as a hedge, specimen, or container plant, having a mature height of about 10 feet and a mature width of about 4 feet. In comparison, *Buxus sempervirens* 'Prostrata' (unpatented) grows to a relatively short height, spreading like a ground cover, and is known to have a mature height of about 3 feet and a spread of about 10 feet. *Buxus sempervirens* 'Graham Blandy' displays a slender and tall growth habit, having a mature height of about 15 feet to 18 feet. *Buxus sempervirens* 'Elegantissima' (unpatented) is variegated, with mature size of about 7 feet tall and 7 feet wide.

The unusually fast growth habit of the new cultivar after asexual propagation from a cutting is particularly noteworthy. For instance, attractive dense columnar plants produced from cuttings in 1-gallon containers commonly assume a height of 18 inches or more, and a width of 4 to 5 inches within 2 years following asexual propagation. The new cultivar's particularly rapid growth habit following propagation renders it well suited for commercial production in containers. Expected size of 5 to 6 year old plantings is about 52 inches high by 18 inches wide.

Asexual reproduction of the new cultivar by the use of cuttings has been carried out at Brackenridge, Pa. and at West Grove, Pa. Such propagation has confirmed that the unique combination of characteristics of the new cultivar has been stably established and is well transmitted to successive generations. The new variety reproduces true to type in successive generations of asexual reproduction.

The new cultivar has been named 'Arctic Emerald'.

BRIEF DESCRIPTION OF THE PHOTOGRAPHS

The accompanying photographs show as nearly true as is reasonably possible to make the same, in color illustrations of this character, typical specimens of the new cultivar.

FIG. 1 is a photograph of several mature "mother" plants of the 'Arctic Emerald' cultivar during April 2004 while being grown outdoors without cover for test purposes in a residential lot concealed from public view in Brackenridge, Pa. The plants had been started as 2½ inch cuttings in the lot in the Summer of 1993, and in the photograph are approximately 7½ feet tall and approximately 36 inches wide. The new cultivar's columnar shape, compact branches and foliage, and dense glossy deep green foliage are illustrated.

Figure 2:
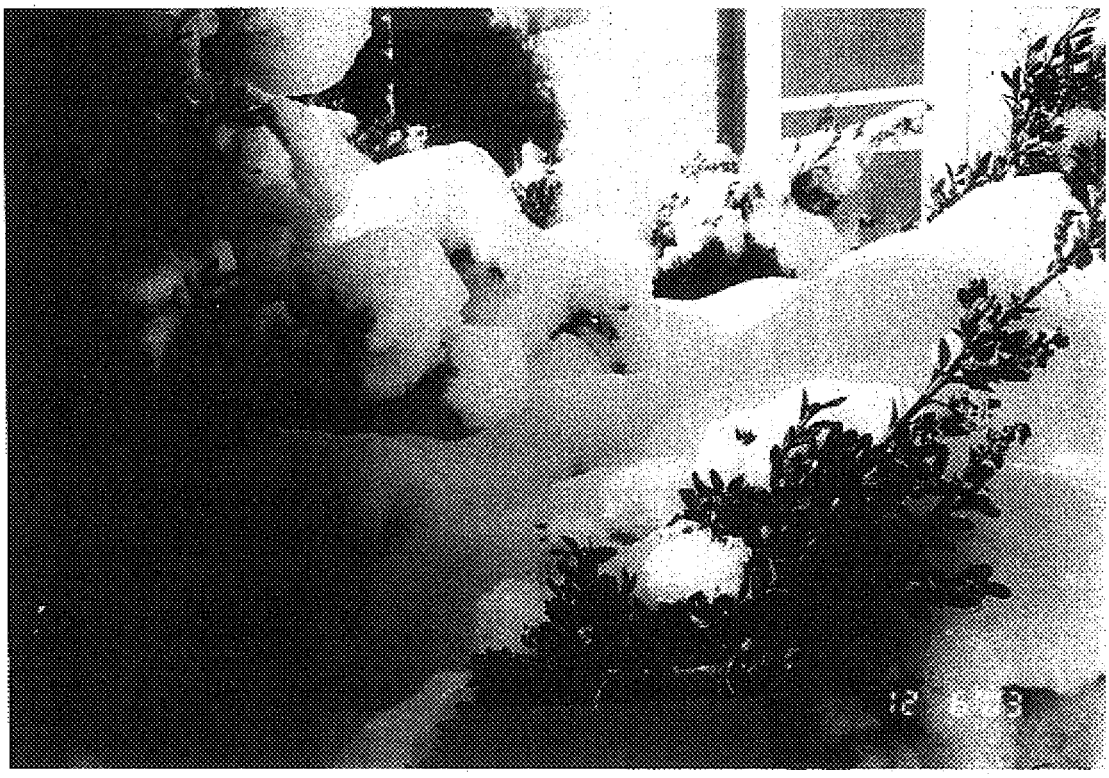

FIG. 2 is a photograph of the same plants as shown in FIG. 1, in the same location, but taken in December 2003. The plants are covered by heavy snow and are nearly bent in half. The bluish tinge to the new cultivar's foliage that is developed in cold weather is illustrated. Comparison of FIGS. 1 and 2 illustrates the 'Arctic Emerald' cultivar's extraordinary cold weather hardiness and tolerance to snow and ice.

Figure 3:
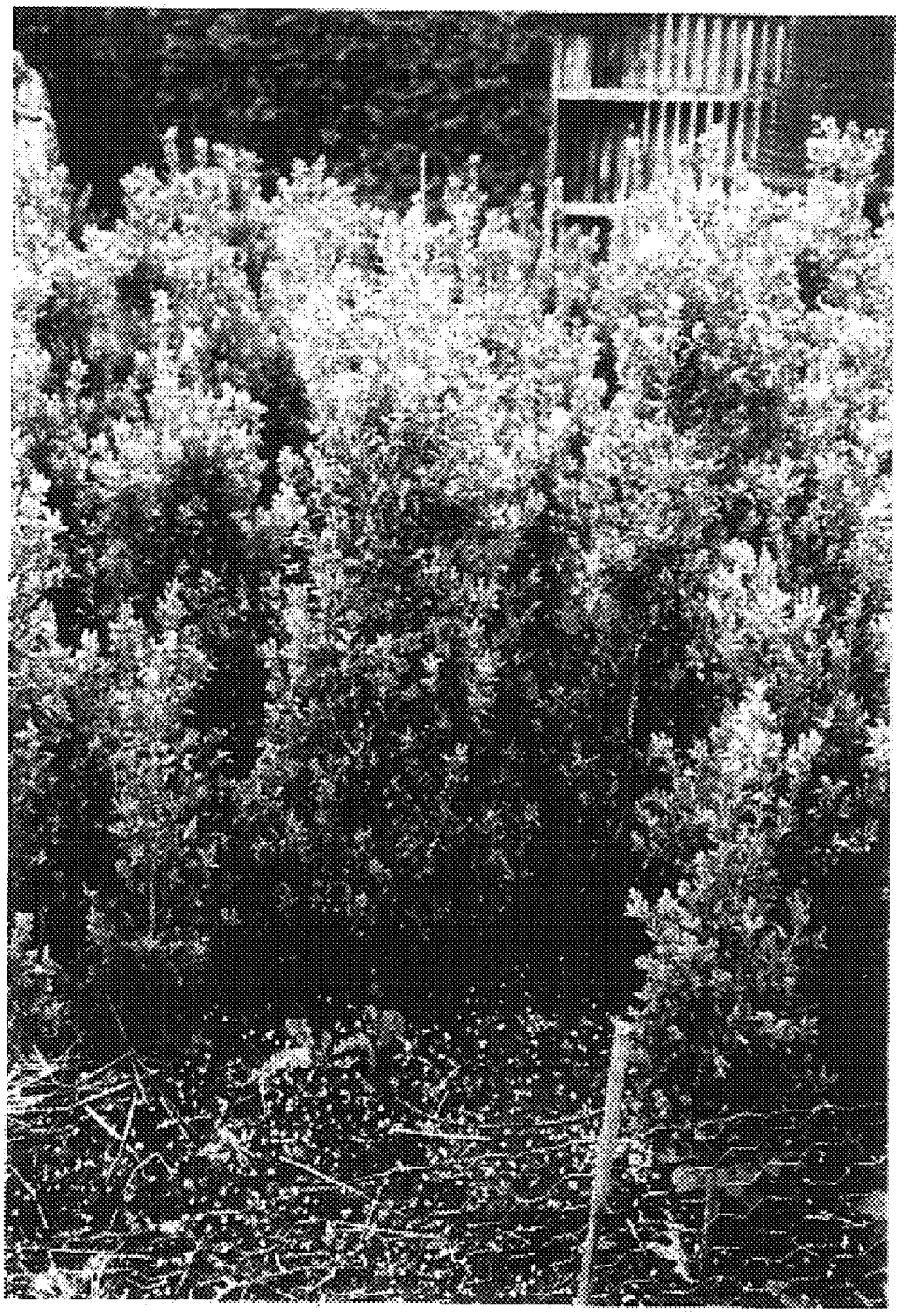

FIG. 3 is a photograph of several 41-month old plants of the 'Arctic Emerald' cultivar during April 2004 while being grown outdoors without cover for test purposes in a residential lot concealed from public view in Brackenridge, Pa. The plants were begun in October 2000 from cuttings in the position illustrated. The new cultivar's columnar, somewhat pyramidal growth habit, dense glossy deep green foliage, and compact branches are illustrated.

Figure 4:
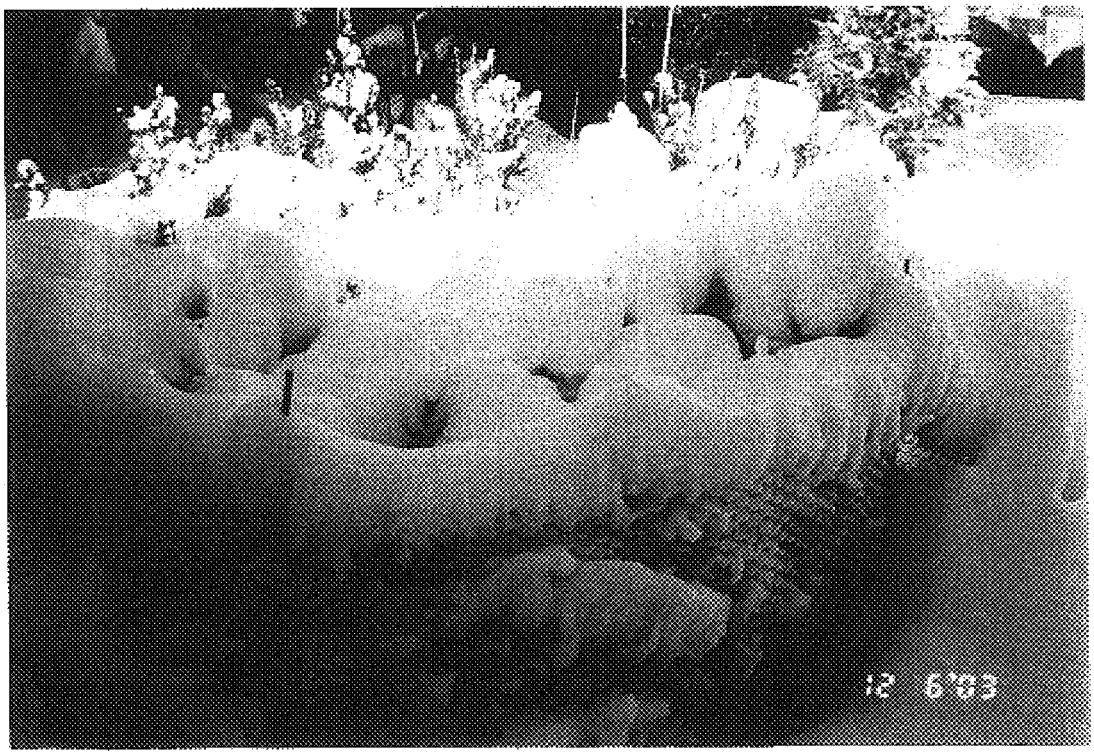

FIG. 4 is a photograph of the same plants as shown in FIG. 3, but was taken in December 2003. The 38-month old plants are shown covered in heavy snow. Comparison of FIGS. 3 and 4 illustrates the 'Arctic Emerald' cultivar's extraordinary cold weather hardiness and tolerance to snow and ice.

Figure 5:
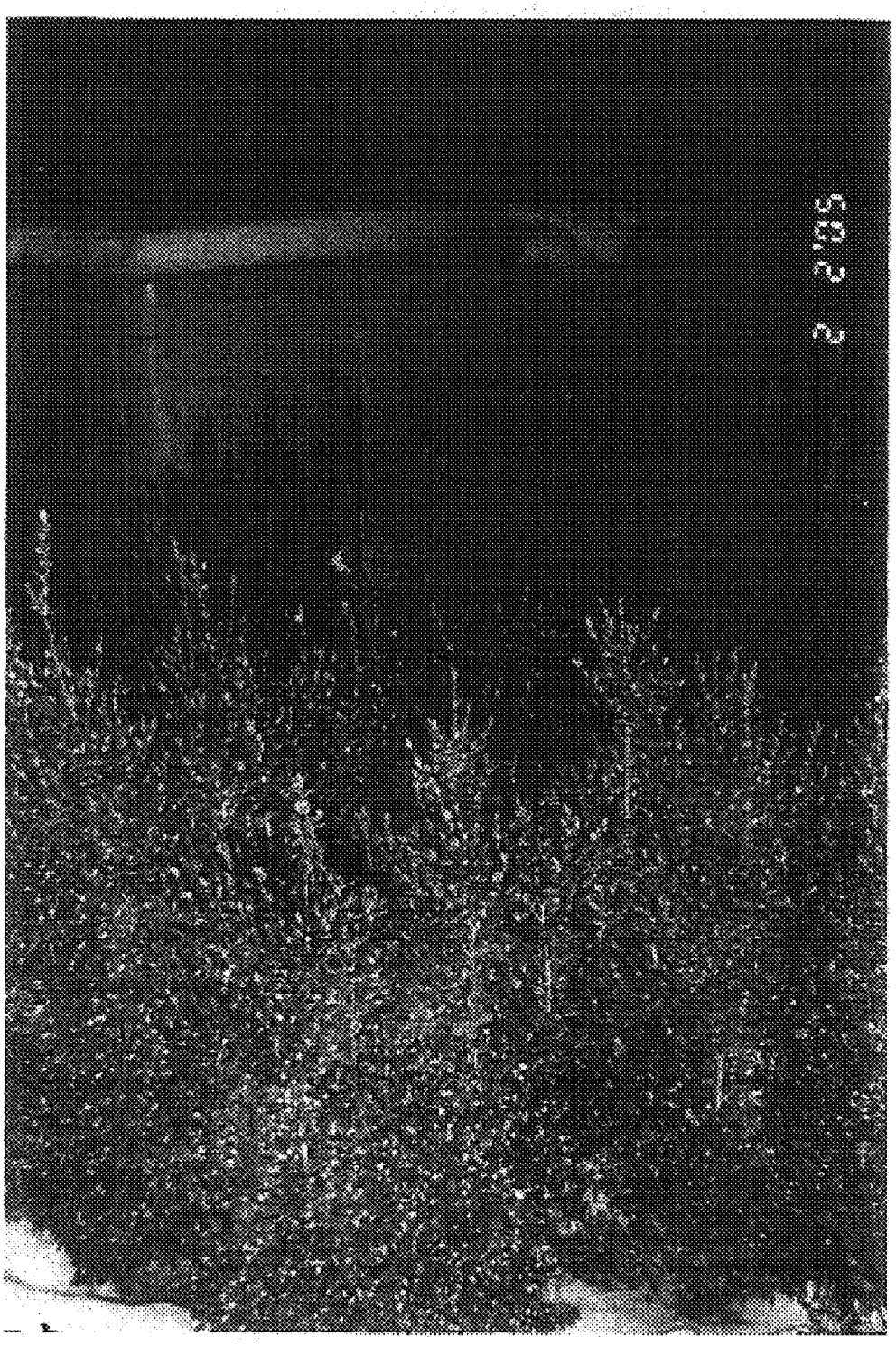

FIG. 5 is a photograph of several 52-month old plants of the 'Arctic Emerald' cultivar during a night in February 2005 while being grown for test purposes in a residential lot concealed from public view in Brackenridge, Pa. The plants had been planted in place in October 2000. The plants are approximately 3½ feet tall and 14 inches wide at their widest point. Despite the single-digit Fahrenheit temperature at the time of the photograph, the plants exhibit their characteristic glossy deep green foliage. The upright dense growth habit in the absence of pruning also is illustrated.

Figure 6:
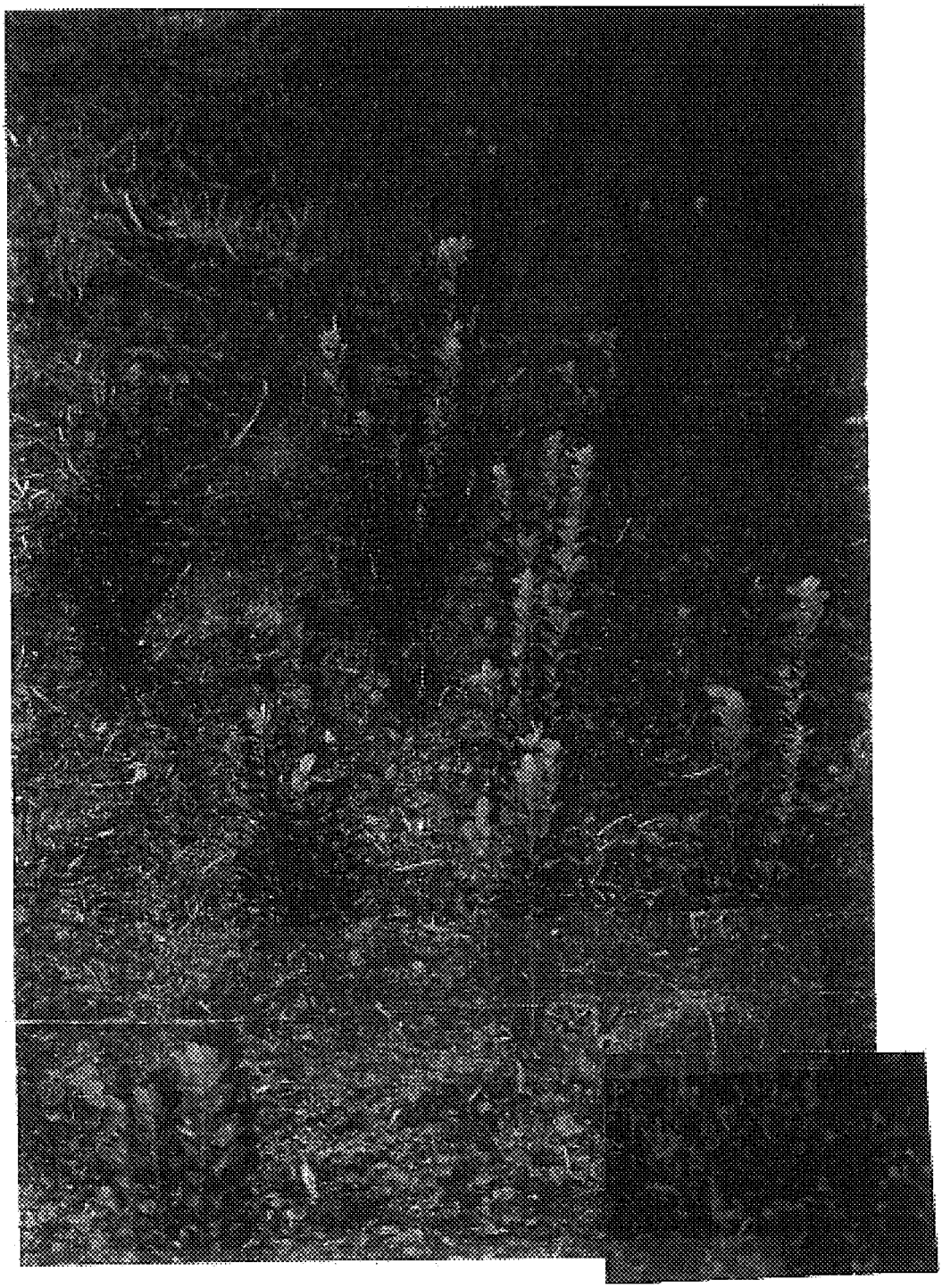

FIG. 6 is a photograph of several 14-month old plants of the new 'Arctic Emerald' cultivar during November 2001 while being grown for test purposes in a test bed concealed from public view in Natrona Heights, Pa. The cultivar's tall columnar growth habit, glossy deep green foliage, and rounded leaf tips are illustrated.

Figure 7:
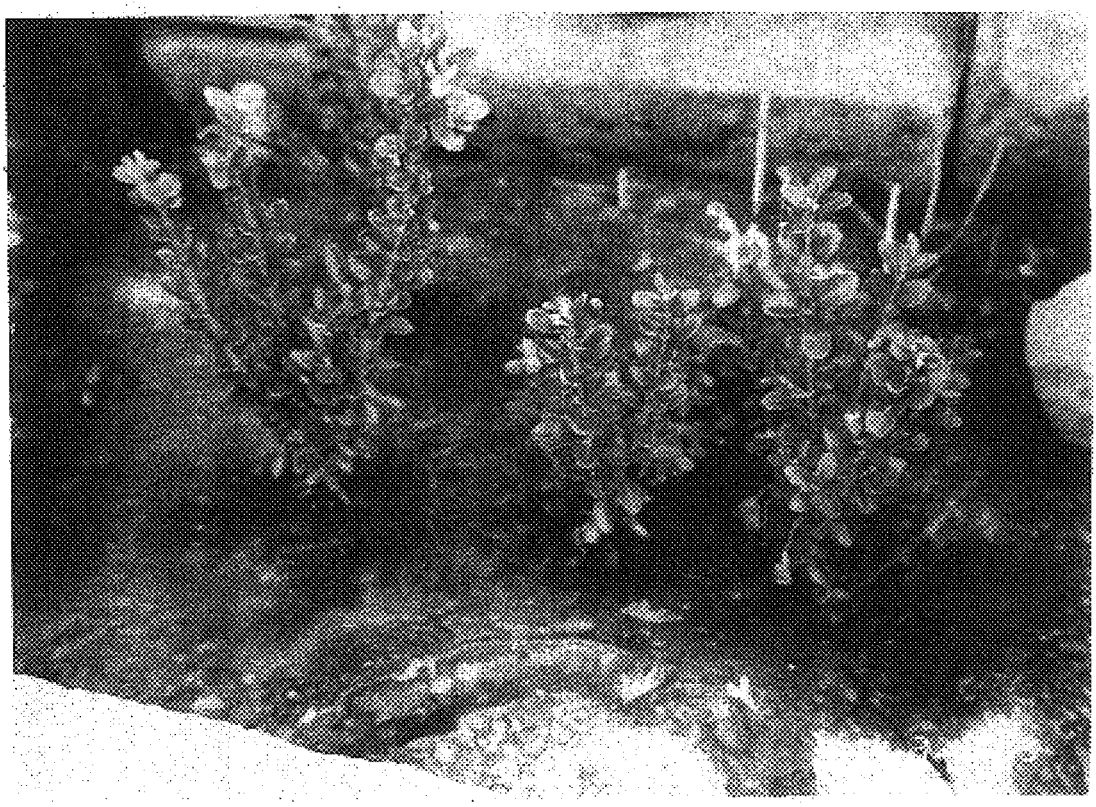

FIG. 7 is a photograph of several plants of the new 'Arctic Emerald' cultivar during March 2003 while being grown in a test bed in a residential lot concealed from public view in Brackenridge, Pa. The plants were started as 2½ inch cuttings planted in the bed 8 months before the photograph was taken. The photograph shows the plants after 3-inch thick ice had covered the test bed and the cultivar's hardy near-surface root system for a period of over two weeks. The plants exhibit a bluish tinge to the glossy deep green foliage. The cultivar's tolerance to and hardiness in cold temperatures and ice are illustrated.

Figure 8:
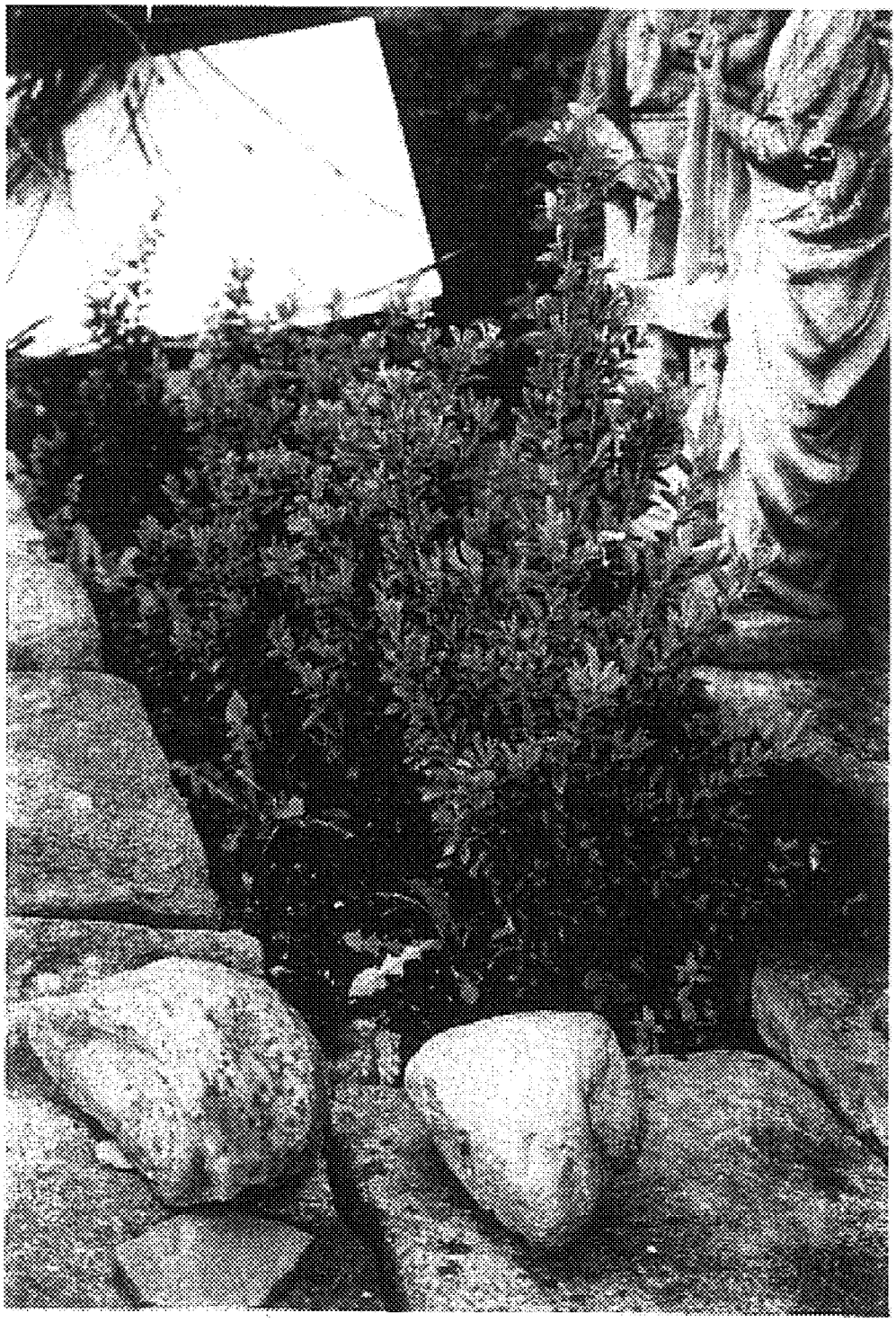

FIG. 8 is a photograph of the same plants as shown in FIG. 7 in the same test bed, but during April 2004. The plants are shown in 21 months old and were grown outdoors without protective cover. The plants evidence no damage from the winter temperatures and ice shown in FIG. 7. Also, the cultivar's columnar growth habit, and glossy deep green and dense foliage are illustrated.

Figure 9:
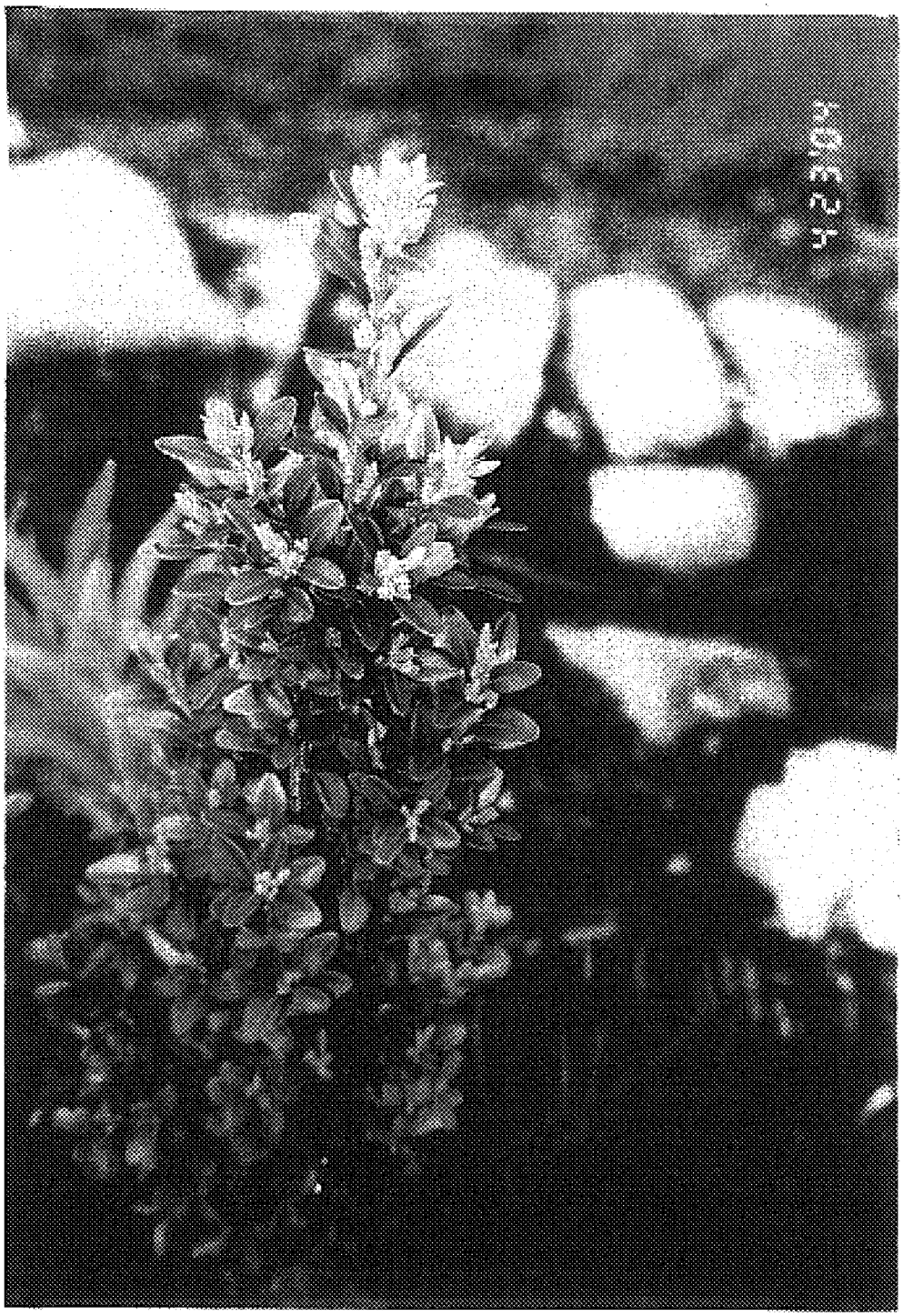

FIG. 9 is a photograph of the 'Arctic Emerald' cultivar during April 2004 which being grown for test purposes in a residential lot concealed from public view in Brackenridge, Pa. The plant is shown approximately 17 months old. The new cultivar's dense foliage, columnar growth habit, and glossy deep green coloration, here with a bluish tinge, are illustrated. The plants is shown with multiple buds of new growth, which contribute to the dense and compact growth habit of the new cultivar.

Figure 10:
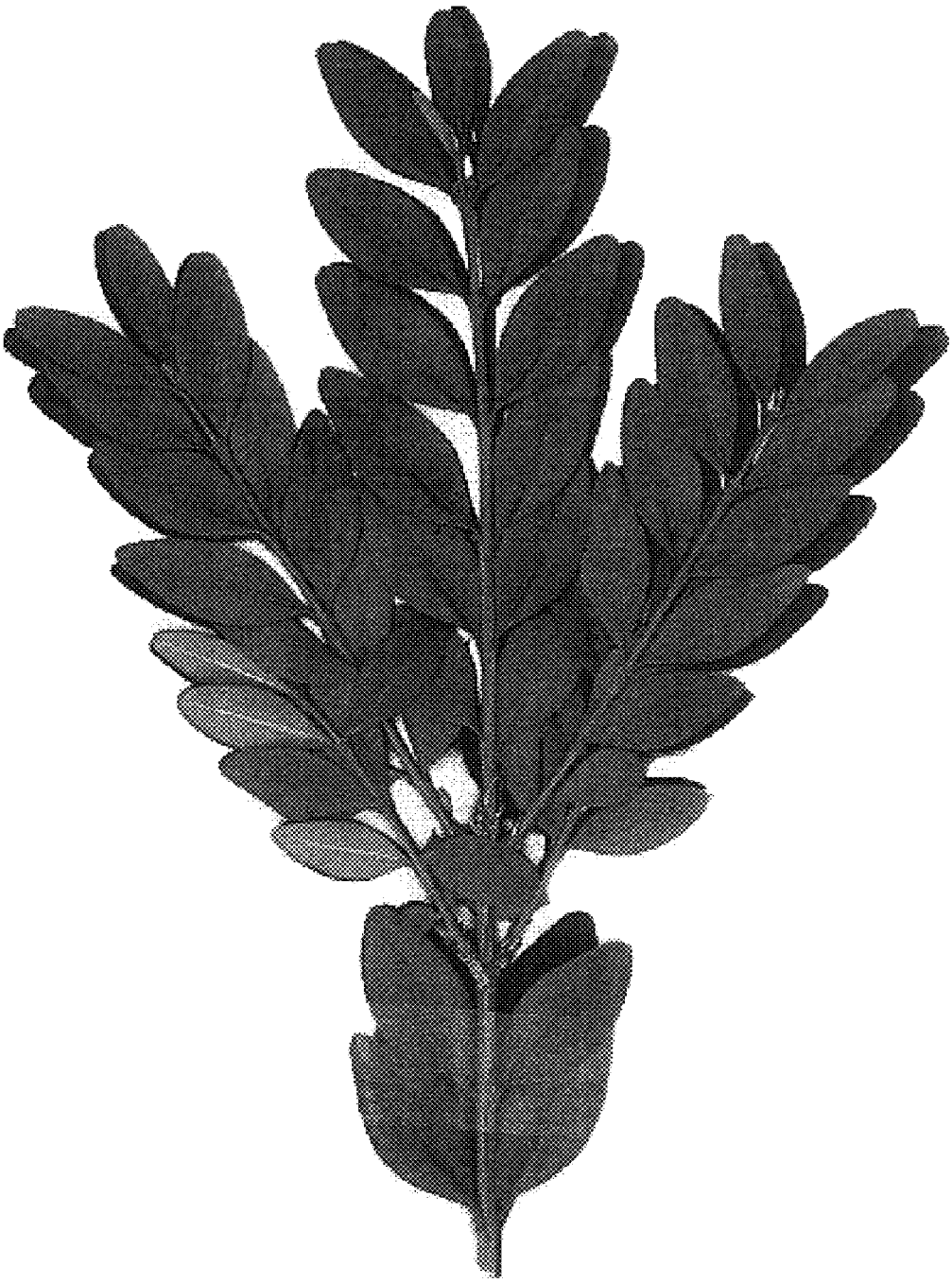

FIG. 10 is a photograph of a cutting from a 54-month old plant of the 'Arctic Emerald' cultivar taken during February 2005 while the plant was being grown for test purposes in a residential lot concealed from public view in Brackenridge, Pa. The temperature was 35° F. at the time the cutting was taken. The new cultivar's deep green foliage with rounded leaf tips, cold weather hardiness, and excellent growth uniformity are illustrated. Three of the four bottommost leaves on the leftmost branch also show the lighter green color of the underside of the foliage.

Figure 11:
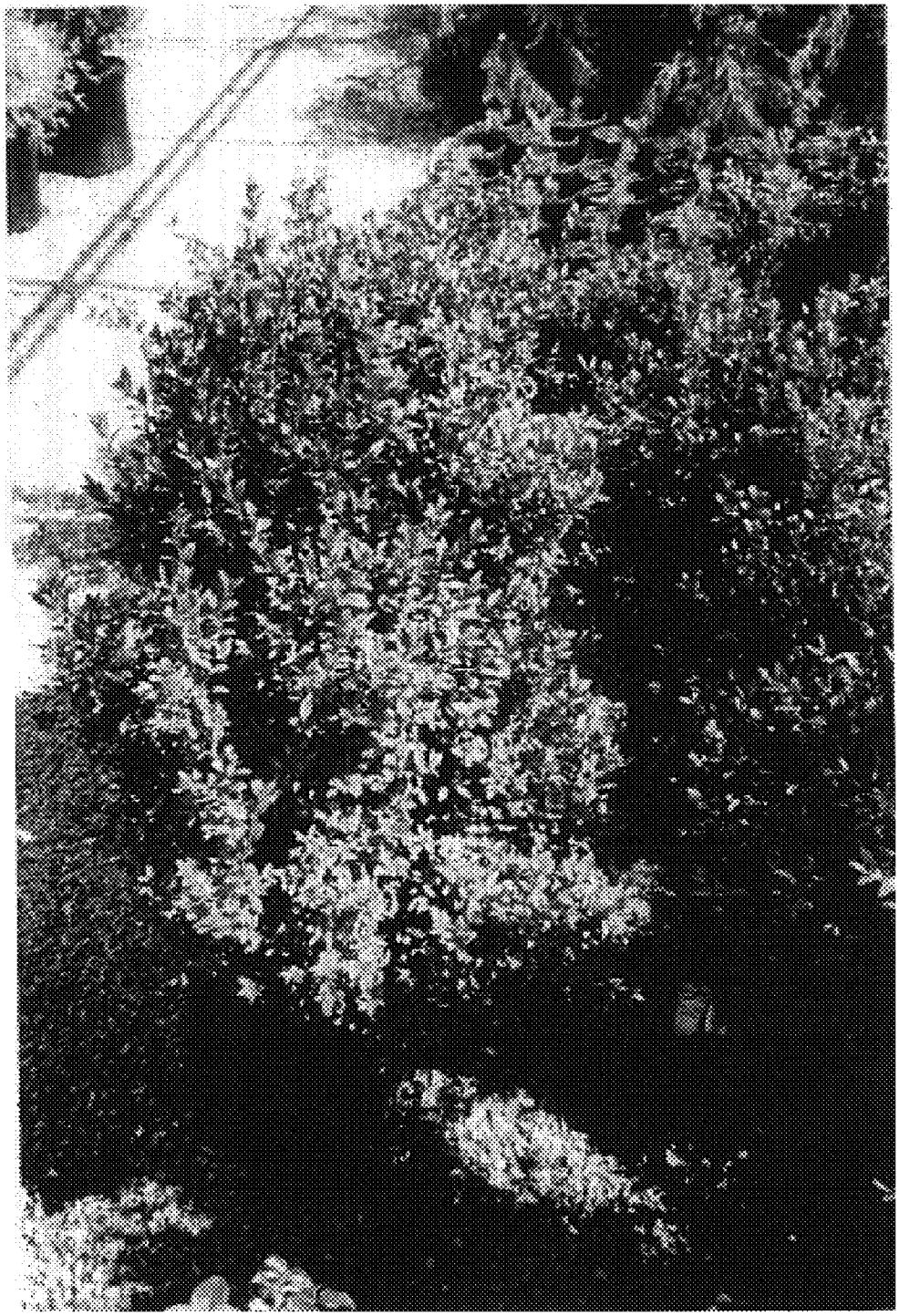

FIG. 11 is a photograph of an approximately 4 year old plant of the 'Arctic Emerald' cultivar taken on Sep. 21, 2005. The plant is shown in a 3 gallon container.

DETAILED DESCRIPTION

The following is a detailed description of the new cultivar of the present invention which was prepared while observing 11½ year old plants growing in a residential lot in Brackenridge, Pa., concealed from public view. Color terminology is in accordance with the R.H.S. Colour Chart of The Royal Horticultural Society, London, England, except where general terms of ordinary dictionary significance are used.

Type: Extraordinarily hardy broad-leaf evergreen shrub with strong hardy near-surface root system, suitable for garden decoration, formal and general landscape use, and container plantings.

Botanical classification: *Buxus sempervirens* cultivar of uncertain parentage, which was discovered in nature around 1993 in Brackenridge, Pa., and was selected and asexually propagated. It is believed that the cultivar may be the result of a naturally occurring whole plant mutation of an existing but unidentified *Buxus* variety (unpatented). The new cultivar has been named 'Arctic Emerald'.

Growth habit: Fast growing, columnar, somewhat pyramidal, dense foliage, and upright, with compact pliable branches. The plant height commonly exceeds plant width, with a common mature plant height-to-width ratio being approximately 7:3. A more rapid growth cycle than most other *Buxus* cultivars commonly is observed, with added growth throughout the Spring and into the Fall growing seasons.

Plant dimensions: 11½ year old plant commonly assumes a height of approximately 7½ feet and a width of approximately 3 feet. Older plants will assume taller height, and a maximum height has not yet been observed. More rapid growth has been observed for plants of 8 years or more.

Propagation: The new cultivar holds its distinguishing characteristics through succeeding propagations by asexual propagation methods, such as the rooting of vegetative cuttings.

Juvenile foliage:

*Size.*—Approximately 0.75 inch in length on average.

*Shape.*—Generally oval-shaped, with a cuneate base and a rounded apex.

*Margin.*—Entire.

*Winter color.*—Upper surface: Yellow-Green Group 147A. Lower surface: Yellow-Green Group 144A with a mid-rib of Green Group 137C.

*Spring color.*—Upper surface: Yellow-Green Group 147A. Lower surface: Yellow-Green Group 144A, with a mid-rib of Green Group 137C.

*Summer color.*—Upper surface: Green Group 137A. Lower surface: Green Group 138B, with a mid-rib of Yellow-Green Group 144A.

*Fragrance.*—None.

*Quantity.*—About 30 or more leaves per 4 inches of branch length.

*Venation.*—Approximately ⅞ inch smooth and glossy veins arranged in an outwardly-directed diagonal slant pattern on both upper surface and underside of leaf. Upper surface: Yellow-Green Group 147 A. Underside: Yellow-Green Group 146A.

Mature foliage:

*Size.*—Approximately 1.25 inches in length on average and approximately 0.5 inch in width on average.

*Shape.*—Generally oval-shaped, with a cuneate base and a generally rounded apex.

*Margin.*—Entire.

*Winter color.*—Upper surface: Yellow-Green Group 147A. Lower surface: Yellow-Green Group 144A, with a mid-rib of Green Group 137C.

*Spring color.*—Upper surface: Yellow-Green Group 147A. Lower surface: Yellow-Green Group 144A, with a mid-rib of Green Group 137C.

*Summer color.*—Upper surface: Green Group 137B. Lower surface: Yellow-Green Group 144A, with a mid-rib of Yellow-Green Group 144A.

*Fragrance.*—None.

*Quantity.*—Approximately 60 leaves per each 5 inches of branch, with extending new patterns of growth providing dense gatherings of new branches and leaves.

*Venation.*—Approximately ⅞ inch smooth and glossy veins arranged in an outwardly-directed diagonal slant pattern on both upper surface and underside of leaf. Upper surface: Yellow-Green Group 147 A. Underside: Yellow-Green Group 146A.

Juvenile stem: May have 1-5 vertical stems. Stems vary from about 4-6.5 inches up to about 22-26 inches in length. Typical internode length is about 3-5 inches. Smooth texture. Color: Green Group 139 A on upper stem and Green Group 139B on lower stem.

Mature stem: Typical length is about 36 inches. Typical internode length is 12 inches. Smooth texture. Color: Green Group 139 A on upper stem and Green Group 139B on lower stem.

Juvenile branches:

*Color.*—Yellow-Green Group 147A.

*Diameter.*—Approximately 0.4 cm on average.

*Number.*—Typically 10-12 branches per plant.

*Internode length.*—Typically 3-5 inches.

*Texture.*—Smooth.

Mature branches:

*Color.*—Green Group 138B.

*Diameter.*—Approximately 1.5 cm on average.

Juvenile petioles: Average length 6 to 8 inches. Average diameter approximately 1/16 inch. Smooth texture. Color: Yellow-Green Group 147B.

Mature petioles: Average length 5 to 9 inches. Average diameter just under 0.125 inch. Smooth texture. Color: Green Group 133B.

Inflorescence: Observed plants of age 8 years old and up to last observation at 11½ years exhibit small non-fragrant clusters of cream-colored blossoms (Yellow-White Group 158D in cold conditions). Each blossom develops into a seed pod of two half-moon shaped seeds per pod. Pods are cream-colored (Grey-Brown Group N 199C) with a straw-like texture, and seeds within a pod are extremely hard and exhibit a cream-colored outer surface (concave side color: Grey-Orange Group 164B; and convex side color: Grey-Orange Group 164C).

Flower buds: Mature flower buds hardy to U.S.D.A. Plant Hardiness Zone 5, and possibly to Zone 4. Average bud diameter is about 0.375 inch. Average bud length is about 0.375 inch. Overall form/shape of buds is an open "burst" pattern. Bud surface is sateen. Color: Yellow-White Group 158D.

Reproductive organs:

*Pistils.*—A single pistil per female flower. Each pistil includes 1 ovary (including 3 fused locules) and 3 free styles (each having a bilobed stigma). Typical ovary length is approximately 2220 micrometers, and typical ovary diameter is approximately 2330 micrometers. Typical style length is approximately 1130 micrometers, and typical style width (at base) is approximately 1200 micrometers. Typical stigma length is approximately 1390 micrometers, and typical stigma width is approximately 1360 micrometers.

*Stamens.*—4 stamens per male flower, each stamen including a filament and an anther. Filament color is RHS Colour Chart Yellow Group 11D, and anther color is RHS Colour Chart Yellow Group 5A. Typical filament length is approximately 2040 micrometers, and typical filament width is approximately 470 micrometers. Typical anther length is approximately 1770 micrometers, and typical anther width is approximately 1270 micrometers.

*Pollen.*—Pollen is abundant, typically with hundreds of pollen grains per stamen. Pollen is RHS Colour Chart Yellow Group 5A.

Development:

*Hardiness.*—Has been tested hardy to U.S.D.A. Plant Hardiness Zone 5, and it is believed it may hardy to Zone 4. As observed at Brackenridge, Pa., the new cultivar has well withstood winter temperatures at least as low as −2° F., wind chill factors of −25° F., wind forces of 55-60 miles per hour, and summer temperatures at least as high 96° F., all without any sign of damage to the foliage or other parts of the plants.

*Disease resistance.*—No disease problems have been observed by the inventor to date.

*Insect tolerance.*—No insect damage has been observed by the inventor to date.

What is claimed:

1. A new and distinct variety of Boxwood plant possessing the following characteristics:

(a) assumes a dense, columnar, somewhat pyramidal, upright growth habit;

(b) lacks typical boxwood foliage fragrance;

(c) exhibits an unusually rapid growth cycle following asexual propagation from a cutting;

(d) exhibits an exceptionally strong root system;

(e) exhibits glossy deep olive green foliage substantially throughout the year in high and low temperatures, and does well in full sun, partial sun, and shade, without any substantial change in coloration during the winter;

(f) exhibits excellent all-season hardiness to at least U.S.D.A. Plant Hardiness Zone 5;

(g) exhibits exceptional tolerance to wind, ice and snow due, at least in part, to the yielding character of its pliable branches;

substantially as herein shown and described.

* * * * *